(12) United States Patent
Notte et al.

(10) Patent No.: US 9,296,632 B2
(45) Date of Patent: Mar. 29, 2016

(54) PHOSPHONATE COMPOUNDS

(75) Inventors: Patrick P. B. Notte, Wavre (BE); Jan H. J. Van Bree, Ottenburg (BE); Albert Devaux, Mont-Saint-Guibert (BE)

(73) Assignee: ITALMATCH CHEMICALS SPA, Genoa (IT)

( * ) Notice: Subject to any disclaimer, the term of this patent is extended or adjusted under 35 U.S.C. 154(b) by 1363 days.

(21) Appl. No.: 12/518,674

(22) PCT Filed: Dec. 11, 2007

(86) PCT No.: PCT/EP2007/063687
§ 371 (c)(1),
(2), (4) Date: Feb. 1, 2010

(87) PCT Pub. No.: WO2008/071692
PCT Pub. Date: Jun. 19, 2008

(65) Prior Publication Data
US 2010/0145066 A1   Jun. 10, 2010

(30) Foreign Application Priority Data

Dec. 11, 2006   (EP) .................................. 06025516

(51) Int. Cl.
C07F 9/22       (2006.01)
C07F 9/28       (2006.01)
C02F 5/12       (2006.01)
C02F 5/14       (2006.01)
C07F 9/38       (2006.01)
C02F 103/10     (2006.01)
C02F 103/28     (2006.01)

(52) U.S. Cl.
CPC ... C02F 5/12 (2013.01); C02F 5/14 (2013.01); C07F 9/3808 (2013.01); *C02F 2103/10* (2013.01); *C02F 2103/28* (2013.01)

(58) Field of Classification Search
CPC .... C02F 2103/10; C02F 2103/28; C02F 5/12; C02F 5/14; C07F 9/3808
USPC ....................... 548/413; 558/158, 159; 562/11
See application file for complete search history.

(56) References Cited

U.S. PATENT DOCUMENTS

| | | | |
|---|---|---|---|
| 558,526 A * | 4/1896 | Strickland .............. | A01C 15/02 222/268 |
| 4,033,896 A | 7/1977 | Mitchell et al. | |
| 5,133,956 A | 7/1992 | Garlich et al. | |
| 5,585,226 A * | 12/1996 | Strickland et al. ............ | 430/393 |

FOREIGN PATENT DOCUMENTS

| | | |
|---|---|---|
| DE | 2423881 A1 | 12/1974 |
| DE | 3601559 A1 | 7/1987 |
| EP | 0330923 A2 | 9/1989 |
| EP | 0772084 A2 | 5/1997 |
| WO | 94/00145 A1 | 1/1994 |

OTHER PUBLICATIONS

STN Nov. 16, 1984.*
STN 1984.*
Database Beilstein [Online] Beilstein Institute for Organic Chemistry, Frankfurt-Main, DE; XP002471159 retrieved from XFIRE Database accession No. BRN 8436669 abstract & Rezik et al; RUSS. CHEM. BL,. vol. 48, No. 5, 1999, pp. 979-983.

* cited by examiner

*Primary Examiner* — Yevegeny Valenrod
*Assistant Examiner* — Blaine G Doletski
(74) *Attorney, Agent, or Firm* — Husch Blackwell LLP

(57) ABSTRACT

Novel phosphonate compounds are disclosed embodying an aminophosphonate moiety and a selected reaction partner. These compounds offer beneficial alternatives, and additional possibilities, to extant phosphonates and are capable of delivering desirable benefits from an application standpoint and from a compatibility standpoint broadly.

12 Claims, No Drawings

PHOSPHONATE COMPOUNDS

CROSS REFERENCE TO RELATED APPLICATIONS

This application is a U.S. National Phase Application of International Application PCT Application No. PCT/EP2007/063687 filed on Dec. 11, 2007, which claims the benefit of priority from European Patent Application No. EP 06025514.8 filed on Dec. 11, 2006. The disclosures of International Application PCT Application No. PCT/EP2007/063687 and European Patent Application No. EP 06025516.3 are incorporated herein by reference.

This invention relates to a defined class of novel phosphonate compounds and to possible applications for such phosphonate compounds. The compounds in accordance with the invention actually combine two moieties, to wit: a reactive phosphonate moiety and a moiety of a class of specific reaction partners as defined in more detail below. The novel compounds can be considered for beneficial use in multiple industrial applications such as dispersion, water-treatment, scale inhibition, sequestration, corrosion inhibition, pharmaceuticals and pharmaceutical intermediates, textiles, detergents, secondary oil recovery, paper industry, sugar and beer industry, fertilizers and micronutrients and metal treatment.

Phosphonate compounds generally have been known for a long time and have been/are used in multiple commercial applications. As one thus can expect, the prior art is well established and fairly crowded.

U.S. Pat. No. 5,879,445 describes the use of compounds containing at least one phosphonic aminoalkylene group and at least one polyalkoxylated chain for fluidizing an aqueous suspension of mineral particles or hydraulic binder paste. WO 94/08913 divulges comparable technologies.

U.S. Pat. No. 4,330,487 describes a process of preparing N,N'-disubstituted methylene phosphonic acids by reacting α,ω-alkylene diamines with formaldehyde and phosphorous acid in aqueous medium in accordance with the Mannich reaction at a pH of generally less than 1. Zaitsev V. N. et al., Russian Chemical Bulletin, (1999), 48(12), 2315-2320, divulges modified silicas containing aminophosphonic acids covalently bonded onto the silica surface.

U.S. Pat. No. 4,260,738 describes starch ether derivatives containing aminophosphonic acid groups, namely either one or two anionic methylene phosphonic acid groups, bound to a cationic nitrogen. The starch derivative is said to exhibit cationic or anionic properties which (properties) may be increased by introducing selected groups together with the aminophosphonic acid reagent. The starch derivatives can be used beneficially as pigment retention aids in paper making processes. U.S. Pat. No. 4,297,299 pertains to novel N-(alkyl)-N-(2-haloethyl)-aminomethylene phosphonic acids exhibiting desirable pigment retention properties upon use in paper making processes. EP-A 0 772 084 discloses a bleach fixing solution comprising a metal complex of a polyamino monosuccinic acid, where the polyamino monosuccinic acid can be a N-phosphonomethyl-N'-monosuccinic acid.

However, known phosphonates, irrespective of desirable application benefits, can be subject to minimal, possibly secondary in relation to the application, negatives including medium compatibility and marginally optimized application suitability. There is thus a standing need to provide application-tailored phosphonate compounds, to yield, in particular, enhanced application benefits while simultaneously minimizing performance distractions and non-desirable interferences.

It is a major object of this invention to provide novel phosphonate compounds suitable for a broad range of selected applications. It is another object of this invention to generate novel phosphonate compounds which can easily and efficiently be synthesized starting from selected reaction partners. Yet another object of this invention aims at providing novel phosphonate compounds by combining selected phosphonate moieties with selected reaction partners to thus yield phosphonate compounds tailored for providing selected application benefits.

The foregoing and other benefits can now be met by means of novel phosphonate compounds embodying, and prepared starting from, a selected reactive phosphonate moiety and a selected reaction partner.

The term "percent" or "%" as used throughout this application stands, unless defined differently, for "percent by weight" or "% by weight". The terms "phosphonic acid" and "phosphonate" are also used interchangeably depending, of course, upon medium prevailing alkalinity/acidity conditions. The term "reactive" phosphonates is merely meant to emphasize the ease with which the phosphonate starting moiety B can be used for synthesizing the claimed phosphonate compounds.

Phosphonate compounds have now been discovered containing a reactive phosphonate moiety and a reaction partner selected from a number of individual species. In more detail, the invention herein relates to novel phosphonate compounds of the general formula:

T-B wherein B is a phosphonate containing moiety having the formula:

—X—N(W)(ZPO$_3$M$_2$)

wherein X is selected from C$_2$-C$_{50}$ linear, branched, cyclic or aromatic hydrocarbon chain,
optionally substituted by a C$_1$-C$_{12}$ linear, branched, cyclic, or aromatic group, (which chain and/or which group can be) optionally substituted by OH, COOH, F, OR' and SR' moieties, wherein R' is a C$_1$-C$_{12}$ linear, branched, cyclic or aromatic hydrocarbon chain; and [A-O]$_x$-A wherein A is a C$_2$-C$_9$ linear, branched, cyclic or aromatic hydrocarbon chain and x is an integer from 1 to 200;
Z is a C$_1$-C$_6$ alkylene chain;
M is selected from H and C$_1$-C$_{20}$ linear, branched, cyclic or aromatic hydrocarbon chains;
W is selected from H, ZPO$_3$M$_2$ and [V—N(K)]$_n$K, wherein V is selected from: a C$_2$-C$_{50}$ linear, branched, cyclic or aromatic hydrocarbon chain, optionally substituted by C$_1$-C$_{12}$ linear, branched, cyclic or aromatic groups, (which chains and/or groups are) optionally substituted by OH, COOH, F, OR' or SR' moieties wherein R' is a C$_1$-C$_{12}$ linear, branched, cyclic or aromatic hydrocarbon chain; and from [A-O]$_x$-A wherein A is a C$_2$-C$_9$ linear, branched, cyclic or aromatic hydrocarbon chain and x is an integer from 1 to 200; and
K is ZPO$_3$M$_2$ or H and n is an integer from 0 to 200; and
wherein T is a moiety selected from the group of:
(i) MOOC—X—N(U)—;
(ii) MOOC—C(X$^2$)$_2$—N(U)—;
(iii) MOOC—X—S—;
(IVi) [X(HO)$_n$(N—U)$_{n'}$]$_{n''}$—;
(Vi) U—N(U)—[X—N(U)]$_{n'''}$;
(VIi) D-S—;
(VIIi) CN—;
(VIIIi) MOOC—X—O—;

(IXi) MOOC—C($X^2$)$_2$—O—;
(Xi) NHR"—; and
(XIi) (DCO)$_2$—N—;
wherein M, Z, W and X are as defined above; U is selected from linear, branched, cyclic or aromatic $C_1$-$C_{12}$ hydrocarbon chains, H and X—N(W)(ZPO$_3$M$_2$); $X^2$ is independently selected from H, linear, branched, cyclic or aromatic $C_1$-$C_{20}$ hydrocarbon chains, optionally substituted by $C_1$-$C_{12}$ linear, branched, cyclic or aromatic hydrocarbon groups, optionally substituted by OH, COOH, R'O, R'S and/or NH$_2$ moieties; n', n" and n'" are independently selected from integers of from 1 to 100; D and R" are independently selected from $C_1$-$C_{50}$ linear, branched, cyclic or aromatic hydrocarbon chains, optionally substituted by a $C_1$-$C_{12}$ linear, branched, cyclic, or aromatic group, (which chain and/or which group can be) optionally substituted by OH, COOH, F, OR' and SR' moieties, wherein R' is a $C_1$-$C_{12}$ linear, branched, cyclic or aromatic hydrocarbon chain; and A'O-[A-O]$_x$-A wherein A is a $C_2$-$C_9$ linear, branched, cyclic or aromatic hydrocarbon chain, x is an integer from 1 to 200 and A' is selected from $C_1$-$C_{50}$ linear, branched, cyclic or aromatic hydrocarbon chain, optionally substituted by a $C_1$-$C_{12}$ linear, branched, cyclic, or aromatic group, (which chain and/or which group can be) optionally substituted by OH, COOH, F, OR' and SR' moieties, wherein R' has the meaning given above; with the further proviso that D can also be represented by H; where the following compounds are excluded: ethylenediamine-N-phosphonomethyl-N'-monosuccinic acid, 1,6-hexamethylenediamine-N-phosphonomethyl-N'-monosuccinic acid, 2-hydroxypropylene-1,3-diamino-N-phosphonomethyl-N'-monosuccinic acid, 1,2-propylenediamine-N-phosphonomethyl-N'-monosuccinic acid, 1,3-propylenediamine-N-phosphonomethyl-N' monosuccinic acid, and ethylene-bis(oxyethylenenitrilo)-N-phosphonomethyl-N'-monosuccinic acid.

The novel phosphonate compounds of this invention actually embody and can, in one execution, be prepared by reacting a phosphonate, corresponding to the general formula Y—X—N(W)(ZPO$_3$M$_2$), with a reaction partner selected from the group of moieties numbered (i)-(XIi). Y in the phosphonate compound represents a substituent the conjugated acid of which has a pKa equal to or smaller than 4.0, preferably equal to or smaller than 1.0.

The pKa value is a well known variable which can be expressed as follows:

pKa=-log$_{10}$ Ka.

wherein Ka represents the thermodynamic equilibrium acidity constant.

The pKa values of all acid substances are known from the literature or can, if this were needed, be determined conveniently.

Y can preferably be selected from Cl, Br, I, HSO$_4$, NO$_3$, CH$_3$SO$_3$ and p-toluene sulfonate and mixtures thereof.

In the definition of X, R', A and V the $C_x$-$C_y$ linear or branched hydrocarbon chain is preferably linear or branched alkane-diyl with a respective chain length. Cyclic hydrocarbon chain is preferably $C_3$-$C_{10}$-cycloalkane-diyl. Aromatic hydrocarbon chain is preferably $C_6$-$C_{12}$-arene-diyl. When the foregoing hydrocarbon chains are substituted, it is preferably with linear or branched alkyl of a respective chain length, $C_3$-$C_{10}$-cycloalkyl, or $C_6$-$C_{12}$-aryl. All these groups can be further substituted with the groups listed with the respective symbols.

More and particularly preferred chain lengths for alkane moieties are listed with the specific symbols. A cyclic moiety is more preferred a cyclohexane moiety, in case of cyclohexane-diyl in particular a cyclohexane-1,4-diyl moiety. An aromatic moiety is preferably phenylene or phenyl, as the case may be, for phenylene 1,4-phenylene is particularly preferred.

The individual moieties in the phosphonate B reaction partner can be beneficially selected from species as follows:

| Moiety | Preferred | Most Preferred |
|---|---|---|
| X | $C_2$-$C_{30}$ | $C_2$-$C_{12}$ |
|  | [A-O]$_x$-A | [A-O]$_x$-A |
| V | $C_2$-$C_{30}$ | $C_2$-$C_{12}$ |
|  | [A-O]$_x$-A | [A-O]$_x$-A |
| wherein for both, X and V independently, | | |
| A | $C_2$-$C_6$, | $C_2$-$C_4$, |
| x | 1-100 | 1-100 |
| Z | $C_1$-$C_3$ | |
| M | H, $C_1$-$C_6$ | H, $C_1$-$C_4$ |
| n | 1-100 | 1-25 |

Specific examples of individual species of the reaction partner T are recited, usually as radicals:
(i) amino acids of the formula MOOC—X—N(U)—;
(ii) α-amino acids of the formula MOOC—C($X^2$)$_2$—N(U)—;
(iii) thioacids of the formula MOOC—X—S—;
(IVi) amino alcohols of the formula [X(HO)$_n$(N—U)$_{n'}$]$_{n''}$— including combined poly and/or mono species;
(Vi) diamines and polyamines corresponding to the formula:

U—N(U)—[X—N(U)]$_{n'''}$—;

(VIi) thiols of the formula D-S—;
(VIIi) cyanide of the formula CN—;
(VIIIi) hydroxyacids of the formula MOOC—X—O—;
(IXi) α-hydroxyacids of the formula MOOC—C($X^2$)$_2$—O—;
(Xi) amines of the formula NHR"—; and
(XIi) imides of the formula (DCO)$_2$—N—.

In preferred species of (ii), $X^2$ can be substituted by any one or more of the following moieties: SR', OR', COOH, NH$_2$ and OH. Examples of the like preferred α-amino acids are glutamic acid, methionine, lysine and threonine. D in (XIi) can be selected independently.

The individual moieties in the T reaction partner can beneficially be selected from the identically termed moieties, inclusive of preferred and most preferred species, recited for the phosphonate B reaction partner. This applies, in particular, to all the structural elements in the partner T formula (e). Additional partner T (vs. B) elements shall have the following meaning.

| Moiety | Preferred | Most Preferred |
|---|---|---|
| $X^2$ | H, $C_1$-$C_{12}$ | H, $C_1$-$C_{10}$ |
| n', n" | 1-50 | 1-25 |
| n'" | 1-100 | 1-50 |
| R" | $C_1$-$C_{30}$ | $C_1$-$C_{16}$ |
|  | A'O-[A-O]$_x$-A | A'O-[A-O]$_x$-A |
| D | $C_1$-$C_{30}$, H | $C_1$-$C_{16}$, H |
|  | A'O-[A-O]$_x$-A | A'O-[A-O]$_x$-A |
| wherein for both, R" and D independently, | | |
| A | $C_2$-$C_6$ | $C_2$-$C_4$ |
| x | 1-100 | 1-100 |
| A' | $C_1$-$C_{30}$ | |
| W | ZPO$_3$M$_2$ | |
| U | H, $C_1$-$C_8$, | as preferred |
|  | —X—N(ZPO$_3$M$_2$) | wherein X is $C_2$-$C_{12}$ and Z is $C_1$-$C_3$ |

Examples of suitable species of the reaction partner T and precursors therefore are listed:

| A | Species | Precursor |
|---|---|---|
| (i) | 6-amino hexanoic acid | H(*) |
| (ii) | aspartic acid; lysine | H |
| (iii) | thioglycolic acid | H, alkali metal |
| (IVi) | poly(amino alcohol) | H |
|  | dipropanolamine | H |
|  | 2-(2-aminoethoxy)ethanol | H |
| (Vi) | poly(ethylene imine) | H |
|  | polyallylamine | H |
| (VIi) | thiol, thiolate | H, alkali metal |
| (VIIi) | cyanide | H, alkali metal |
| (VIIIi) | hydroxy acid | H |
| (IXi) | α-hydroxy acid | H |
| (Xi) | amine | H |
| (XIi) | imide | H, alkali metal |

(*)unless the corresponding lactam is used.

The amine moiety in (Vi) can be incorporated into the hydrocarbon chain, like linear polyethylene imine, or can be attached, via a single bond, to the alkyl chain, like in polyallylamine, or can be a mixture of both configurations, like in branched polyethylene imine. The same applies to the nitrogen and oxygen in (IVi). In particular, oxygen, identified as OH, can be part of the hydrocarbon chain or can be attached to that chain through a single bond or can be a mixture of both configurations.

The hydrocarbon moiety of reaction partner T can comprise and can be represented by normal and branched species. As an example, the term "butyl" can represent any one of known isomers and as such can stand for: n-butyl; iso-butyl; sec-butyl; and t-butyl. Along the same lines, the definition of partner T containing optical carbon atoms refers to any one of the isomers i.e. D species, L species, D,L species and combinations thereof.

In one aspect of this invention, preferred species of reaction partner T can be selected from the group of: (i); (ii); (IVi); (Vi); (Xi); and (XIi). Examples of the like preferred species are represented by:
(i): caprolactam or 6-amino hexanoic acid; 2-pyrrolidone or 4-amino butanoic acid; and lauryl lactam or 12-amino dodecanoic acid;
(ii): glutamic acid; methionine; lysine; aspartic acid; phenylalanine; glycine; and threonine;
(IVi): 2-ethanol amine; 6-amino hexanol; 4-amino butanol; di-(2-ethanolamine); 2-(2-aminoethoxy)ethanol; and 3-propanol amine;
(Vi): diaminotoluene; 1,6-hexamethylene diamine; 1,4-butane diamine; 1,2-ethylene diamine; linear or branched polyethylene imine; and polyallylamine;
(Xi): methylamine; ethylamine; propylamine; butylamine; hexylamine; heptylamine; octylamine; nonylamine; decylamine; dodecylamine; aniline; and $C_{12}$-$C_{22}$ fatty amines including linear and branched species; and
(XIi): phthalimide; succinimide; and maleimide.

In another aspect of the invention, preferred species of reaction partner T can be selected from the group of: (iii); (VIi); (VIIIi); and (IXi). Examples of the like preferred species are represented by:
(iii): thioglycolic acid; and cysteine;
(VIi): methylthiol; ethylthiol; propylthiol; pentylthiol; hexylthiol; octylthiol; thiophenol; thionaphthol; decylthiol; and dodecylthiol;
(VIIIi): 3-hydroxy propanoic acid; 4-hydroxy butanoic acid; 5-hydroxy pentanoic acid; and 2-hydroxy acetic acid; and
(IXi): tartaric acid; hydroxysuccinic acid; and α-hydroxy isobutyric acid.

In a preferred embodiment of the invention, in compounds (i) X in group T is not $CH(COOH)$—$CH_2$ and in the compounds
(ii) $CX^2{}_2$ is not —$CH(CH_2$—$COOH)$—.

In a particularly preferred embodiment of the invention, the group (i) is a group $$MOOC—X'—N(U)— \quad (i')$$

wherein
X' is $CH_2$—$CH_2$—, —$CH(CH_3)$—$CH_2$—, —$(CH_2)_3$—, —$(CH_2)_5$—, or —$(CH_2)_{11}$—, and
M and U have the meaning given above;
and/or
the group (ii) is a group $$MOOC—C(X^{2'})_2—N(U)— \quad (ii')$$

wherein
—$C(CX^{2'})_2$— is —$CH_2$—, —$CH(CH_3)$—, —$CH(CH(CH_3)_2)$—, —$CH(CH_2$—$CH(CH_3)_2)$—, —$CH(CH(CH_3)(C_2H_5))$—, —$CH(CH_2$—$CH_2$—$S$—$CH_3)$—, —$CH(CH_2OH)$—, —$CH(CH(OH)$—$CH_3)$—, —$CH(CH_2$—$SH)$—, —$CH(CH_2$—$CH_2$—$COOH)$—, or —$CH(CH_2$—$CH_2$—$CH_2$—$NH_2)$— and
M and U have the meanings given above.

The phosphonate compounds herein can be prepared by means of conventional measures routinely available in the relevant domain. In one approach, the reactive phosphonate and a reaction partner can be combined, in an aqueous medium, by adding stoichiometric proportions of both species, thereby taking into consideration the required degree of substitution. A process for the manufacture of the phosphonate compounds of the invention comprises reacting a phosphonate compound having the general formula $Y$—$X$—$N(W)(ZPO_3M_2)$ wherein Y is a substituent the conjugated acid of which has a pKa equal to or smaller than 4, preferably equal to or smaller than 1, with a reactant selected from the group of i-XIi, in aqueous medium, having a pH of 7 or higher, frequently a pH in the range of from 8-14, at a temperature generally above 0° C., usually in the range of from 10° C. to 200° C., preferably 50° C. to 140° C. Higher reaction temperatures can be used subject to adequate pressure containment e.g. by means of standard pressure vessels.

The pH value is measured in the reaction medium at the reaction temperature. In a preferred execution, the manufacturing method is conducted in the presence of an alkali metal iodide such that the molar ratio of the T moiety to the iodide is in the range of from 5000:1 to 1:1. The iodine ions act as a catalyst to thus facilitate the reaction of the B moiety with the reaction partner T. The presence of a minimal level of the iodide ions leads to the in situ formation of a more reactive, as compared to e.g. the corresponding chloro structure, derivative.

Recovery of the phosphonate is preferably effected by methods known per se to someone skilled in the art. For example, the free phosphonic acids can be precipitated by acidification of the reaction mixture, e.g. with concentrated hydrochloric acid, filtered off, washed and dried. Further purification can, e.g. be effected by recrystallisation, or chromatographic methods.

The phosphonates T-B of the invention are preferably used in the chemical and pharmaceutical industry, the textile industry, oil industry, paper industry, sugar industry, beer industry, the agrochemical industry and in agriculture.

Preferred uses are as dispersants, water treatment agents, scale inhibitors, pharmaceuticals and pharmaceutical intermediates, detergents, secondary oil recovery agents, fertilizers and micronutrients (for plants).

The phosphonate compounds in accordance with the invention are illustrated by means of Examples I-XX. To that effect a phosphonate moiety B precursor is reacted with a reaction partner T precursor as follows Polyamines.

I:

146.65 g (0.50 mole) of 96% pure 3-chloro propyl imino bis(methylene phosphonic acid) were added under stirring over 100 minutes to a mixture of 29.25 g of linear polyethylene imine (Mw=423, 0.66 mole based on —$CH_2$—$CH_2$—$NH_2$ unit) with 160.8 g (2.01 moles) of 50% sodium hydroxide and 100 g of water while maintaining the temperature between 35° C. and 40° C. When addition was complete, the mixture was heated at reflux for 7 hours. $^{31}P$ NMR analysis of the crude product indicated 92% of polymer bound propyl imino bis(methylene phosphonic acid) with 7% of the 3-hydroxy propyl imino bis(methylene phosphonic acid) (HOPIBMPA).

II:

146.65 g (0.50 mole) of 96% pure 3-chloro propyl imino bis(methylene phosphonic acid) were added under stirring over 100 minutes to a mixture of 19.5 g of linear polyethylene imine (Mw=423, 0.44 mole based on —$CH_2$—$CH_2$—$NH_2$ unit) with 160.8 g (2.01 moles) of 50% sodium hydroxide and 100 g of water while maintaining the temperature between 35 and 40° C. When addition was complete, the mixture was heated at reflux for 7 hours. $^{31}P$ NMR analysis of the crude product indicated 93% of polymer bound propyl imino bis(methylene phosphonic acid) with 5% of the hydroxy propyl imino bis(methylene phosphonic acid) (HOPIBMPA).

Amino Acids.

III:

7.51 g (0.1 mole) of glycine were mixed with 1.9 g (0.011 mole) of potassium iodide and 8 g (0.1 mole) of 50% sodium hydroxide and 30 ml of water. A second solution was prepared by mixing under cooling 58.65 g (0.2 mole) of 96% pure 3-chloro propyl imino bis(methylene phosphonic acid) with 32 g (0.4 mole) of 50% sodium hydroxide and 100 ml of water. The two solutions were mixed together under stirring while controlling the temperature at 10° C. Another 32 g (0.4 mole) of 50% sodium hydroxide were added to this mixture which was heated under stirring to 100° C. for 5 hours. $^{31}P$ NMR analysis of the crude product showed 60% of the glycine N,N-bis(propyl imino bis[methylene phosphonic acid]) and 12.3% of the corresponding mono-adduct.

IV:

15.02 g (0.2 mole) of glycine were mixed with 2.05 g (0.012 mole) of potassium iodide and 16 g (0.2 mole) of 50% sodium hydroxide and 30 ml of water (Solution 1). A second solution was prepared by mixing under cooling 58.65 g (0.2 mole) of 96% pure 3-chloro propyl imino bis(methylene phosphonic acid) with 32 g (0.4 mole) of 50% sodium hydroxide and 100 ml of water. The two solutions were mixed under stirring while controlling the temperature at 10° C. Another 32 g (0.4 mole) of 50% sodium hydroxide were added to this mixture which was heated under stirring to 100° C. for 5 hours. $^{31}P$ NMR analysis of the crude product showed 43.5% of the glycine N,N-bis(propyl imino bis[methylene phosphonic acid]) and 44.5% of the corresponding mono-adduct.

V:

35.6 g (0.4 mole) of D,L-alanine were mixed with 32 g (0.4 mole) of 50% sodium hydroxide and 40 ml of water under cooling at 10° C. 117.3 g (0.4 mole) of 96% pure 3-chloro propyl imino bis(methylene phosphonic acid) were mixed with 150 ml of water and with 32 g (0.4 mole) of 50% sodium hydroxide diluted with water to a volume of 100 ml at 10° C. (solution 1). Another solution was prepared by diluting 120 g (1.50 moles) of 50% sodium hydroxide in 300 ml of water (solution 2). Solutions 1 and 2 were added simultaneously under stirring to the D,L-alanine solution while controlling the temperature at 10° C. Reaction mixture was further heated for 6 hours between 80 and 100° C. $^{31}P$ NMR analysis of the crude product showed 72.6% of the D,L-alanine N-[propyl imino bis(methylene phosphonic acid)]; 16.2% of the corresponding di-adduct and 9.2% w/w of the 3-hydroxy propyl imino bis(methylene phosphonic acid).

VI:

44.5 g (0.5 mole) of β-alanine were mixed with 50 ml of water and 40 g (0.5 mole) of 50% sodium hydroxide. 146.61 g (0.5 mole) of 96% pure 3-chloro propyl imino bis(methylene phosphonic acid) were mixed with 150 ml of water and 80 g (1 mole) of 50% sodium hydroxide under cooling at 10° C. The β-alanine solution was added to the 3-chloro propyl imino bis(methylene phosphonic acid) under stirring and cooling at 10° C. Another 80 g (1 mole) of 50% sodium hydroxide and 2 g (0.012 mole) of potassium iodide were added to this mixture which was heated under stirring to 100° C. for 4 hours. $^{31}P$ NMR analysis of the crude product showed 54.8% w/w of the β-alanine N,N-bis[propyl imino bis(methylene phosphonic acid)]; 43.1% of the corresponding mono-adduct and 2.1% of the 3-hydroxy propyl imino bis(methylene phosphonic acid).

VII:

26.7 g (0.3 mole) of β-alanine were mixed with 35 ml of water and 24 g (0.3 mole) of 50% sodium hydroxide. 175.98 g (0.6 mole) of 96% pure 3-chloro propyl imino bis(methylene phosphonic acid) were mixed with 250 ml of water and 96 g (1.2 mole) of 50% sodium hydroxide under cooling at 10° C. The β-alanine solution was added to the 3-chloro propyl imino bis(methylene phosphonic acid) under stirring and cooling at 10° C. Another 96 g (1.2 mole) of 50% sodium hydroxide were added to this mixture which was heated under stirring to 100° C. for 6 hours. $^{31}P$ NMR analysis of the crude product showed 80.6% w/w of the β-alanine N,N-bis[propyl imino bis(methylene phosphonic acid)]; 6.7% of the corresponding mono-adduct and 3.7% of the 3-hydroxy propyl imino bis(methylene phosphonic acid).

VIII:

58.85 g (0.4 mole) of glutamic acid were mixed with 40 ml of water and 64 g (0.8 mole) of 50% sodium hydroxide. 117.3 g (0.4 mole) of 96% pure 3-chloro propyl imino bis(methylene phosphonic acid) were mixed with 150 ml of water and 32 g (0.4 mole) of 50% sodium hydroxide under cooling at 10° C. (solution 1). 120 g (1.5 moles) of 50% sodium hydroxide were diluted with water to prepare a 300 ml solution (solution 2). Solutions 1 and 2 were simultaneously added under stirring to the glutamic acid solution at 10° C. This mixture was heated under stirring to 100° C. for 6 hours. $^{31}P$ NMR analysis of the crude product showed 8.7% w/w of the glutamic acid N,N-bis[propyl imino bis(methylene phosphonic acid)]; 72.8% of the corresponding mono-adduct and 12.9% of the 3-hydroxy propyl imino bis(methylene phosphonic acid).

IX:

53.24 g (0.4 mole) of aspartic acid were mixed with 50 ml of water and 64 g (0.8 mole) of 50% sodium hydroxide. 117.32 g (0.4 mole) of 96% pure 3-chloro propyl imino bis (methylene phosphonic acid) were mixed with 150 ml of water and 64 g (0.8 mole) of 50% sodium hydroxide under cooling at 10° C. L-aspartic acid solution was added under stirring and cooling at 10° C. to the 3-chloro propyl imino bis(methylene phosphonic acid) solution. At the end of the addition, another 64 g (0.8 mole) of 50% sodium hydroxide and 2 g (0.012 mole) of potassium iodide were added to the reaction mixture. This mixture was then heated under stirring to 100° C. for 9 hours. $^{31}$P NMR analysis of the crude product showed 14.5% w/w of the aspartic acid N,N-bis[propyl imino bis(methylene phosphonic acid)]; 76.9% of the corresponding mono-adduct and 4.6% of the 3-hydroxy propyl imino bis(methylene phosphonic acid).

X:

39.93 g (0.3 mole) of aspartic acid were mixed with 40 ml of water and 48 g (0.6 mole) of 50% sodium hydroxide. 175.9 g (0.6 mole) of 96% pure 3-chloro propyl imino bis(methylene phosphonic acid) were mixed with 230 ml of water and 96 g (1.2 mole) of 50% sodium hydroxide under cooling at 10° C. L-aspartic acid solution was added under stirring and cooling at 10° C. to the 3-chloro propyl imino bis(methylene phosphonic acid) solution. Another 96 g (1.2 moles) of 50% sodium hydroxide with 2 g (0.012 mole) of potassium iodide were added to the reaction mixture which was then heated under stirring to 100° C. for 5 hours. $^{31}$P NMR analysis of the crude product showed 51.5% w/w of the aspartic acid N,N-bis[propyl imino bis(methylene phosphonic acid)]; 25.3% of the corresponding mono-adduct and 7.2% of the 3-hydroxy propyl imino bis(methylene phosphonic acid).

XI:

7.51 g (0.1 mole) of glycine were mixed with 30 ml of water and 8 g (0.1 mole) of 50% sodium hydroxide. 55.7 g (0.2 mole) of 96% pure 2-chloro ethyl imino bis(methylene phosphonic acid were mixed with 150 ml of water and 15 g (0.1875 mole) of 50% sodium hydroxide under stirring at 10° C. (solution 1). 53 g (0.6625 mole) of 50% sodium hydroxide were diluted with water to a volume of 110 ml (solution 2). Solutions 1 and 2 were added to the glycine solution under stirring at 10° C. Reaction mixture was further heated between 90 and 100° C. for 4 hours. $^{31}$P NMR analysis of the crude reaction mixture showed 74% of the glycine N,N-bis[ethyl imino bis(methylene phosphonic acid)]; 7.1% of the corresponding mono-adduct and 4.8% of the 2-hydroxy ethyl imino bis(methylene phosphonic acid).

XII:

17.8 g (0.2 mole) of D,L-alanine were mixed with 20 ml of water. 55.7 g (0.2 mole) of 96% pure 2-chloro ethyl imino bis(methylene phosphonic acid) were mixed with 200 ml of water (solution 1). 96 g (1.2 moles) of 50% sodium hydroxide were mixed with 250 ml of water (solution 2). Solutions 1 and 2 were added to the alanine suspension at 10° C. The reaction mixture was heated at 55° C. for 2 hours. $^{31}$P NMR analysis of the crude reaction mixture showed 79.3% of the D,L-alanine N-ethyl imino bis(methylene phosphonic acid); 9.8% of the corresponding di-adduct and 4.2% of the 2-hydroxy ethyl imino bis(methylene phosphonic acid).

XIII:

21.02 g (0.2 mole) of L-serine were mixed with 50 g of water. 55.7 g (0.2 mole) of 2-chloro ethyl imino bis(methylene phosphonic acid were mixed with 150 ml of water and 15 g (0.1875 mole) of 50% sodium hydroxide under stirring and at 10° C. (Solution 1). 69 g (0.8625 mole) of 50% sodium hydroxide were diluted in water to 100 ml (Solution 2). Solutions 1 and 2 were added at 10° C. under stirring to the L-serine suspension. The reaction mixture was further heated at 95° C. for 4 hours. $^{31}$P NMR analysis of the crude reaction mixture showed 81.1% of serine N-ethyl imino bis(methylene phosphonic acid) and 7.9% of the corresponding di-adduct.

Alcohols.

XIV:

18.8 g (0.2 mole) of phenol were mixed with 100 ml of water and 32 g (0.4 mole) 50% sodium hydroxide. 58.65 g (0.2 mole) of 96% pure 3-chloro propyl imino bis(methylene phosphonic acid) were mixed with 100 ml of water and 32 g (0.4 mole) of 50% sodium hydroxide under cooling at 10° C. The phenol solution was gradually added to the 3-chloro propyl imino bis(methylene phosphonic acid) solution under stirring at 10° C. A further 24 g (0.3 mole) of 50% sodium hydroxide were added to this reaction mixture which was heated at 100° C. for 6 hours. Upon cooling the derived 3-phenoxy propyl imino bis(methylene phosphonic acid) was precipitated by addition of 80 ml of concentrated chlorhydric acid. After filtration, washing and drying $^{31}$P NMR analysis confirmed product identity and indicated a purity of 98% w/w. The yield of the isolated product was 65%.

Thiols.

XV:

40.48 g (0.2 mole) of dodecyl thiol were mixed with 150 ml of ethanol, 50 ml of water and 16 g (0.2 mole) of 50% sodium hydroxide. 58.65 g (0.2 mole) of 96% pure 3-chloro propyl imino bis(methylene phosphonic acid were mixed with 100 ml of water and 16 g (0.2 mole) of 50% sodium hydroxide under stirring at 10° C. (solution 1). 48 g (0.6 mole) of 50% sodium hydroxide were mixed with water to get a 70 ml solution (solution 2). Solutions 1 and 2 were simultaneously added to the thiol solution under stirring between 65 and 75° C. Reaction mixture was further heated for 2 hours at 80° C. Upon cooling the derived 3-dodecylthio propyl imino bis(methylene phosphonic acid) was precipitated by addition of 66 ml of concentrated chlorhydric acid. After filtration, washing and drying $^{31}$P NMR analysis confirmed product identity and indicated a purity of 85% w/w with 15% of the dodecyl thiol.

XVI:

40.48 g (0.2 mole) of dodecyl thiol were mixed with 150 ml of ethanol, 50 ml of water and 16 g (0.2 mole) of 50% sodium hydroxide. 55.7 g (0.2 mole) of 96% pure 2-chloro ethyl imino bis(methylene phosphonic acid were mixed with 75 ml of water and 15 g (0.1875 mole) of 50% sodium hydroxide under stirring at 10° C. (solution 1). 49 g (0.6125 mole) of 50% sodium hydroxide were mixed with water to get a 75 ml solution (solution 2). Solutions 1 and 2 were simultaneously added to the thiol solution under stirring between 60 and 70° C. Reaction mixture was further heated for 1 hour at 80° C. Upon cooling the derived 2-dodecylthio ethyl imino bis(methylene phosphonic acid) was precipitated by acidification using concentrated chlorhydric acid. After filtration, washing and drying $^{31}$P NMR analysis confirmed product identity and indicated a purity of 94%.

Thio Acid.

XVII:

18.42 g (0.2 mole) of thioglycolic acid were mixed with 20 ml of water and 16 g (0.2 mole) of 50% sodium hydroxide. 58.65 g (0.2 mole) of 96% pure 3-chloro propyl imino bis(methylene phosphonic acid were mixed with 100 ml of water and 32 g (0.4 mole) of 50% sodium hydroxide under stirring at 10° C. The thioglycolic acid solution was added to the 3-chloro propyl imino bis(methylene phosphonic acid) solution under stirring at 10° C. A further 52 g (0.65 mole) of 50% sodium hydroxide were added to the reaction mixture which was heated to 95° C. for 5 hours. $^{31}$P NMR analysis of the crude product showed 96% of the thioglycolic acid S-propyl imino bis(methylene phosphonic acid) and 4% of the 3-hydroxy propyl imino bis(methylene phosphonic acid).

XVIII:

36.85 g (0.4 mole) of thioglycolic acid were mixed with 40 ml of water and 32 g (0.4 mole) of 50% sodium hydroxide. 114.4 g (0.4 mole) of 96% pure 2-chloro ethyl imino bis (methylene phosphonic acid were mixed with 150 ml of water and 30 g (0.375 mole) of 50% sodium hydroxide under stirring at 10° C. (Solution 1). 146 g (1.825 moles) of 50% sodium hydroxide were diluted with water to a volume of 250 ml (Solution 2). Solutions 1 and 2 were simultaneously added to the thioglycolic acid solution under stirring at 10° C. The reaction mixture was heated to 65° C. for 4 hours. $^{31}$P NMR analysis of the crude product showed 93% of the thioglycolic acid S-ethyl imino bis(methylene phosphonic acid) and 5% of the 2-hydroxy ethyl imino bis(methylene phosphonic acid).

XIX:

24.23 g (0.2 mole) of L-cysteine were mixed with 25 ml of water and 32 g (0.4 mole) of 50% sodium hydroxide. 55.7 g (0.2 mole) of 96% pure 2-chloro ethyl imino bis(methylene phosphonic acid) were mixed with 75 ml of water and 15 g (0.1875 mole) of 50% sodium hydroxide under stirring at 10° C. (Solution 1). 65 g (0.8125 mole) of 50% sodium hydroxide were diluted with water to a total volume of 200 ml (Solution 2). Solutions 1 and 2 were added to the L-cysteine solution with good stirring at 10° C. The reaction mixture was then heated for 2 hours at 55° C. $^{31}$P NMR analysis of the crude product showed 95% of the cysteine S-ethyl imino bis(methylene phosphonic acid) and 5% of the 2-hydroxy ethyl imino bis(methylene phosphonic acid).

Alkanolamine.

XX:

15.27 g (0.25 mole) of ethanolamine were mixed with 10 ml of water. At 10° C., 146.65 g (0.5 mole) of 96% pure 3-chloro propyl imino bis(methylene phosphonic acid) were added to the ethanol amine solution with 80 g (1 mole) of 50% sodium hydroxide. Another 80 g (1 mole) of 50% sodium hydroxide were added at 10° C. with 2 g (0.012 mole) of potassium iodide. The reaction mixture was then heated at 75° C. for 6 hours.

$^{31}$P NMR analysis of the crude product showed 8.8% of the 2-(3-imino bis[methylene phosphonic acid]amino propyl) hydroxy ethane; 71.7% of the 2-bis(3-imino bis[methylene phosphonic acid]amino propyl) hydroxy ethane and 4.1% of the 3-hydroxy propyl imino bis(methylene phosphonic acid).

The Examples illustrate the scope of the invention and also show that the novel phosphonate compounds can easily be prepared in very good yields and purities.

The invention claimed is:

1. A phosphonate compound of the general formula:

T-B wherein B is a phosphonate containing moiety having the formula:
—(CH$_2$)$_3$—N—(CH$_2$PO(OH)$_2$)$_2$ or —(CH$_2$)$_2$—N—(CH$_2$PO(OH)$_2$)$_2$ and wherein T is a moiety having a formula selected from the group consisting of:
(i) MOOC—X—N(U)—;
(ii) MOOC—C(X$^2$)$_2$—N(U)—;
(iii) MOOC—X—S—;
(IVi) [X(HO)$_n$(N—U)$_n$']$_{n'}$—;
(XIV) H$_5$C$_6$—O—
(XX) HO—(CH$_2$)$_2$—NH—
wherein X is selected from C$_2$-C$_{50}$ linear or branched hydrocarbon chain, optionally substituted by a C$_1$-C$_{12}$ linear or branched group, which chain and/or which group can be optionally substituted by OH and COOH moieties; and [A-O]$_x$-A wherein A is a C$_2$-C$_9$ linear or branched hydrocarbon chain and x is an integer from 1 to 200;

Z is a C$_1$-C$_6$ alkylene chain;

M is selected from H and C$_1$-C$_{20}$ linear, branched, cyclic or aromatic hydrocarbon chains;

W is selected from H, ZPO$_3$M$_2$ and [V—N(K)]$_n$K, wherein V is selected from: a C$_2$-C$_{50}$ linear, branched, cyclic or aromatic hydrocarbon chain, optionally substituted by C$_1$-C$_{12}$ linear, branched, cyclic or aromatic groups, which chains and/or groups are optionally substituted by OH, COOH, F, OR' or SR' moieties wherein R' is a C$_1$-C$_{12}$ linear, branched, cyclic or aromatic hydrocarbon chain; and from [A-O]$_x$-A wherein A is a C$_2$-C$_9$ linear, branched, cyclic or aromatic hydrocarbon chain and x is an integer from 1 to 200; K is ZPO$_3$M$_2$ or H and n is an integer from 0 to 200;

U is selected from linear, branched, cyclic or aromatic C$_1$-C$_{12}$ hydrocarbon chains, H and X—N(W)(ZPO$_3$M$_2$); X$^2$ is independently selected from H, linear or branched C$_1$-C$_{20}$ hydrocarbon chains, optionally substituted by C$_1$-C$_{12}$ linear or branched hydrocarbon groups, optionally substituted by OH, COOH, R'O, R'S and/or NH$_2$ moieties; n', n" and n'" are independently selected from integers of from 1 to 100; R" is selected from C$_1$-C$_{50}$ linear, branched, cyclic or aromatic hydrocarbon chains, optionally substituted by a C$_1$-C$_{12}$ linear, branched, cyclic, or aromatic group, which chain and/or which group can be optionally substituted by OH, COOH, F, OR' and SR' moieties, wherein R' is a C$_1$-C$_{12}$ linear, branched, cyclic or aromatic hydrocarbon chain; and A'O-[A-O]$_x$-A wherein A is a C$_2$-C$_9$ linear, branched, cyclic or aromatic hydrocarbon chain, x is an integer from 1 to 200 and A' is selected from C$_1$-C$_{50}$ linear, branched, cyclic or aromatic hydrocarbon chain, optionally substituted by a C$_1$-C$_{12}$ linear, branched, cyclic, or aromatic group, which chain and/or which group can be optionally substituted by OH, COOH, F, OR' and SR' moieties, wherein R' has the meaning given above.

2. The phosphonate compound in accordance with claim 1 wherein T is selected from the group of (i), (ii), (IVi).

3. The phosphonate compound in accordance with claim 2 wherein T is selected from:
(i): caprolactam or 6-amino hexanoic acid; 2-pyrrolidone or 4-amino butanoic acid; and lauryl lactam or 12-amino dodecanoic acid;
(ii): glutamic acid; methionine; lysine; aspartic acid; phenylalanine; glycine; and threonine;
(IVi): 2-ethanol amine; 6-amino hexanol; 4-amino butanol; di-(2-ethanolamine); dipropanolamine; 2-(2-aminoethoxy) ethanol; and 3-propanol amine.

4. The phosphonate compound in accordance with claim 1, wherein T is selected from:
HOOC—(CH$_2$)$_n$—NH—;
HOOC—CH(CH$_3$)—NH—;
HOOC—(CH$_2$)$_2$CH(COOH)—NH—;
HOOC—CH$_2$—(HOOC)CH—NH—;
HOOC—CH(CH$_2$OH)—NH—;
HOOC—CH$_2$—S—;
HO—(CH$_2$)—NH—.

5. The phosphonate compound in accordance with claim 1, wherein U is —(CH$_2$)$_3$—N—(CH$_2$PO(OH)$_2$)$_2$ or —(CH$_2$)$_2$—N—(CH$_2$PO(OH)$_2$)$_2$.

6. The phosphonate compound in accordance with claim 1 wherein phosphonate B has the formula wherein X is C$_2$-C$_{30}$ or $[A-O]_x$-A; V is $C_2$-$C_{30}$ or $[A-O]_x$-A, wherein for both, X and V independently, A is $C_2$-$C_6$ and x is 1-100; Z is $C_1$-$C_3$; M is H or $C_1$-$C_6$; and n is 100.

7. The phosphonate compound in accordance with claim 1 has the formula wherein: $X^2$ is H or $C_1$-$C_{12}$; n' and n" are independently 1-50; n''' is 1-100; R" is $C_1$-$C_{30}$ or A'O-$[A-O]_x$-A; D is H, $C_1$-$C_{30}$ or A'O-$[A-O]_x$-A, wherein for R", A is $C_2$-$C_6$, x is 1-100 and A' is $C_1$-$C_{30}$, W is $ZPO_3M_2$; and U is H, $C_1$-$C_8$, or —X—N—$(ZPO_3M_2)_2$.

8. The phosphonate compound in accordance with claim 1 wherein the phosphonate B has the formula wherein X is $C_2$-$C_{12}$ or $[A-O]_x$-A; V is $C_2$-$C_{12}$ or $[A-O]_x$-A, wherein for both, X and V independently, A is $C_2$-$C_4$ and x is 1-100; M is H or $C_1$-$C_4$; and n is 1-25.

9. The phosphonate compound in accordance with claim 1 wherein the phosphonate B has the formula wherein: $X^2$ is H or $C_1$-$C_{10}$; n', n" are independently 1-25; n''' is 1-50; R" is $C_1$-$C_{16}$ or A'O-$[A-O]_x$-A; D is H, $C_1$-$C_{16}$ or A'O-$[A-O]_x$-A, wherein for both, R" and D independently, A is $C_2$-$C_4$ and x is 1-100; X is $C_2$-$C_{12}$; and Z is $C_1$-$C_3$.

10. The phosphonate compound in accordance with claim 1 wherein T is selected from the group of (iii).

11. The phosphonate compound in accordance with claim 1 wherein T is selected from:
(iii): thioglycolic acid; and cysteine.

12. A dispersant, water treatment agent, scale inhibitor, pharmaceutical, intermediate, detergent, secondary oil recovery agent, fertilizer or micronutrient comprising phosphonate compound according to claim 1.

* * * * *